(12) United States Patent
Wegener et al.

(10) Patent No.: US 10,525,249 B2
(45) Date of Patent: Jan. 7, 2020

(54) SYSTEM AND METHOD FOR CREATING STERILE CONNECTIONS USING ULTRAVIOLET LIGHT

(71) Applicant: Fenwal, Inc., Lake Zurich, IL (US)

(72) Inventors: Christopher J. Wegener, Libertyville, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 228 days.

(21) Appl. No.: 15/448,751

(22) Filed: Mar. 3, 2017

(65) Prior Publication Data

US 2017/0252550 A1  Sep. 7, 2017

Related U.S. Application Data

(60) Provisional application No. 62/304,423, filed on Mar. 7, 2016.

(51) Int. Cl.
   *A61M 39/16*  (2006.01)
   *A61L 2/10*  (2006.01)
   (Continued)

(52) U.S. Cl.
   CPC .............. *A61M 39/16* (2013.01); *A61L 2/10* (2013.01); *F16K 7/045* (2013.01); *F16L 33/28* (2013.01);
   (Continued)

(58) Field of Classification Search
   CPC ........ A61M 39/16; A61M 39/18; F16L 33/28; A61L 2/10; F16K 7/045
   See application file for complete search history.

(56) References Cited

U.S. PATENT DOCUMENTS 4,214,586 A  7/1980 Mericle
4,242,310 A * 12/1980 Greff .................. A61J 1/20
                                                    312/1

(Continued)

FOREIGN PATENT DOCUMENTS

EP          0 459 599 A1   12/1991
WO       WO 85/00979 A1    3/1985
WO     WO 2015/157662 A1   10/2015

OTHER PUBLICATIONS

Extended European search report dated Jul. 25, 2017 for European Patent application No. 17159027.6.-1664.

*Primary Examiner* — Regina M Yoo
(74) *Attorney, Agent, or Firm* — Cook Alex Ltd.

(57) ABSTRACT

A device for connecting first and second medical fluid flow systems includes a linear movement carriage system that is positioned within a housing. The carriage system includes first and second connector holders configured to hold first and second connectors of the first and second medical fluid flow systems, respectively. A coupler holder is configured to hold a coupler and is positioned substantially between the first and second connector holders. The first and second connector holders and the coupler holder are relatively moveable between a separated configuration, where the first and second connectors and the coupler are located in relatively spaced apart positions, and a joined configuration, where the first and second connectors engage the coupler. An ultraviolet light source is positioned in the housing so as to irradiate first and second connectors and the coupler. A drive system transitions the first and second connector holders and the coupler holder between the separated and the joined configurations.

11 Claims, 13 Drawing Sheets

(51) Int. Cl.
 *F16K 7/04* (2006.01)
 *F16L 33/28* (2006.01)
 *A61M 39/10* (2006.01)

(52) U.S. Cl.
 CPC ............. *A61M 2039/1072* (2013.01); *A61M 2039/167* (2013.01)

(56) References Cited

U.S. PATENT DOCUMENTS

| | | | | |
|---|---|---|---|---|
| 4,336,223 A * | 6/1982 | Hillman | ................... | A61L 2/10 210/103 |
| 4,356,394 A * | 10/1982 | Cobean | ................... | A61J 1/00 141/1 |
| 4,433,244 A * | 2/1984 | Hogan | ................... | A61L 2/10 250/455.11 |
| 4,473,369 A * | 9/1984 | Lueders | ............ | A61M 39/1011 285/419 |
| 4,475,900 A * | 10/1984 | Popovich | ................. | A61L 2/10 604/28 |
| 4,500,788 A * | 2/1985 | Kulin | ....................... | A61L 2/10 250/455.11 |
| 4,541,829 A * | 9/1985 | Munsch | ................... | A61J 1/20 141/330 |
| 4,655,762 A * | 4/1987 | Rogers | ................. | A61M 39/16 128/912 |
| 4,774,415 A * | 9/1988 | Biegel | ...................... | A61L 2/08 250/455.11 |
| 4,840,621 A * | 6/1989 | Larkin | ................. | A61M 39/18 141/330 |
| 4,882,496 A * | 11/1989 | Bellotti | ................... | A61M 1/28 250/455.11 |
| 6,245,570 B1 * | 6/2001 | Grimm | ...................... | A61J 1/10 250/453.11 |
| 9,492,574 B2 * | 11/2016 | Rasooly | ............. | A61M 1/1696 |
| 2003/0017073 A1 * | 1/2003 | Eckhardt | ................. | A61L 2/10 422/24 |
| 2005/0209563 A1 * | 9/2005 | Hopping | ................ | A61M 1/28 604/151 |
| 2009/0012451 A1 * | 1/2009 | Sobue | ...................... | A61L 2/10 604/29 |
| 2009/0257910 A1 * | 10/2009 | Segal | ....................... | A61L 2/08 422/22 |
| 2012/0209168 A1 | 8/2012 | Katsuyoshi et al. | | |
| 2014/0334974 A1 * | 11/2014 | Rasooly | ............. | A61M 1/1696 422/24 |

\* cited by examiner

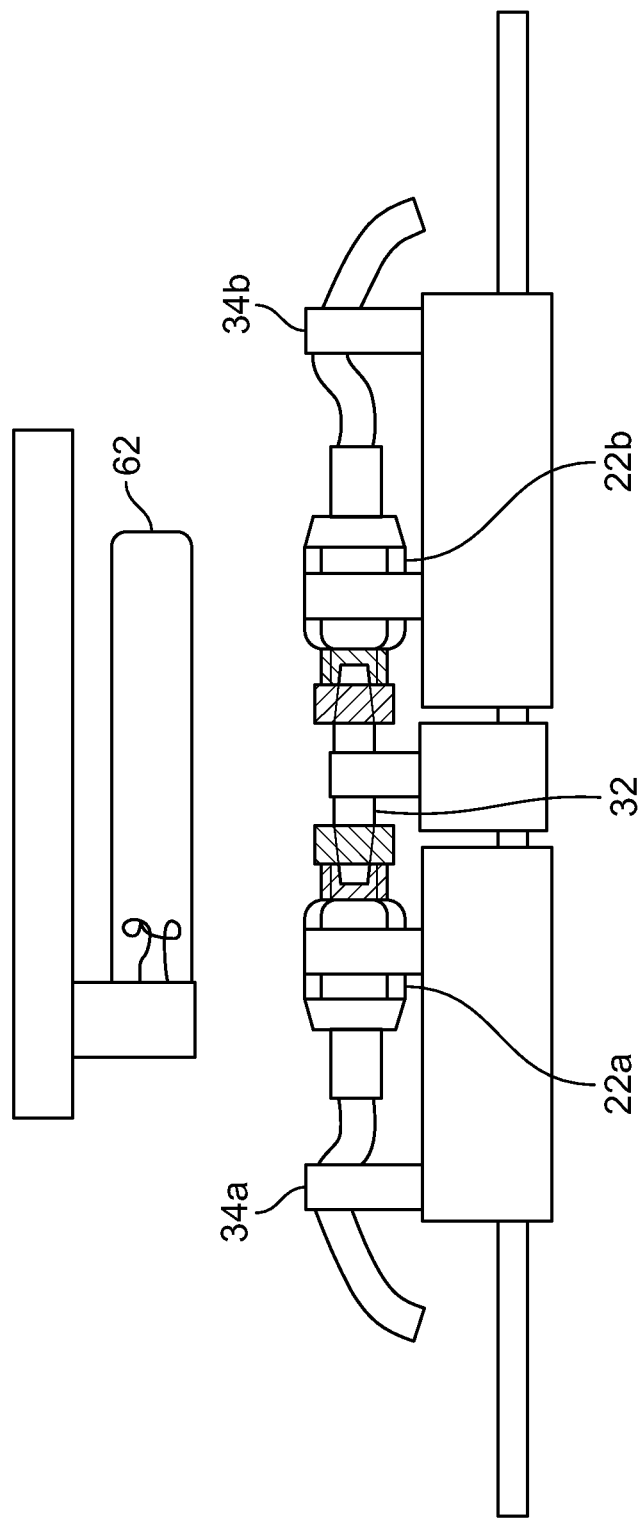

SYSTEM AND METHOD FOR CREATING STERILE CONNECTIONS USING ULTRAVIOLET LIGHT

CLAIM OF PRIORITY

This application claims the benefit of U.S. Provisional Application No. 62/304,423, filed Mar. 7, 2016, the contents of which are hereby incorporated by reference.

FIELD OF THE INVENTION

The present disclosure relates generally to needleless connectors for medical fluid flow systems and, in particular, to a system and method for creating sterile connections using such connectors.

BACKGROUND

Medical fluid flow tubing systems often employ needleless connectors, such as Luer connectors, to reduce the risk of needle stick for employees and to ensure that sealed connections are made. The female half of two mating connectors typically has a septum or silicon valve that covers, or is positioned within, a Luer tapered opening that communicates with a fluid flow path. The male connector features a tapered member having a Luer taper that corresponds to the Luer taper of the female connector with a fluid flow passage therein that communicates with an opening at the tip or distal end of the tapered male member.

Current common practice for making fluid flow connections using needleless connectors is an aseptic process where the exterior surface of the valve, diaphragm or septum of the female connector is manually swabbed with antiseptic prior to insertion of the male connector (which compresses and opens the valve). Manual swabbing requires increased vigilance and discipline by the healthcare professionals attending to a patient or carrying out the process in question. Failure to follow rigorous procedures can potentially result in microorganisms or other contaminants being inadvertently introduced into the fluid path. Even for specialized care in controlled environments, training and existing connector design cannot completely eliminate the possibility of human error for contamination when such a process is used.

Other solutions for connecting medical fluid flow tubing recognize that irradiation of connectors with ultraviolet light provides an antibacterial effect on, or sterilization of, the irradiated connector surfaces. Examples of such systems and devices are presented in U.S. Pat. No. 4,500,788 to Kuhn et al.; U.S. Pat. No. 4,503,333 to Kuhn et al. and U.S. Pat. No. 4,883,496 to Bellotti et al. The systems and devices of these references, however, are intended for use in specialized settings with connectors of special design.

There are a variety of other sterile connection systems for joining fluid flow tubing with specialized connector systems or relatively expensive disposable components. For example, a tubing connector that employs heated wafers is known as the SCD® IIB sterile tubing welder available from Terumo BCT of Lakewood, Colo., and is described in U.S. Pat. No. 4,753,697. Other sterile connection systems may be found in U.S. Patent Application Publication No. US 2014/0077488; U.S. Pat. Nos. 4,157,723 and 5,009,446.

Accordingly, there continues to be a desire to develop advanced systems and methods for creating sterile connections.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a device is provided for connecting first and second medical fluid flow systems, where each includes, respectively, first and second connectors connectable to a coupler. The device includes a housing that is substantially non-transmissive of ultraviolet light. A linear movement carriage system is positioned within the housing and includes a first connector holder configured to hold the first connector, a second connector holder configured to hold the second connector and a coupler holder configured to hold the coupler. The coupler holder is positioned substantially between the first and second connector holders. The first and second connector holders and the coupler holder are relatively moveable between separated and joined configurations. In the separated configuration, the first and second connector holders and the coupler holder are located in relatively spaced apart positions so that first and second connectors held by the first and second connector holders are spaced apart from a coupler held by the coupler holder. In the joined configuration, the first and second connector holders are positioned more closely to the coupler holder than when in the separated configuration so that the first and second connectors held by the first and second connector holders engage the coupler held by the coupler holder. An ultraviolet light source is positioned in the housing so as to irradiate first and second connectors held by the first and second connector holders and a coupler held by the coupler holder when the carriage system is in the separated configuration. A drive system includes a first motor operatively connected to at least one of the first and second connector holders so as to transition the first and second connector holders and the coupler holder between the separated and the joined configurations.

In another aspect, a method is provided for connecting first and second medical fluid flow systems, each of which includes, respectively, first and second connectors connectable to a coupler. The method includes positioning the coupler between the first and second connectors in a spaced-apart position within a substantially ultraviolet non-transmissive housing. The coupler and the first and second connectors are irradiated with ultraviolet light. The first and second connectors and the coupler are relatively moved so that the first and second connectors connectably engage the coupler. The connected first and second connectors and the coupler are removed from the housing.

In yet another aspect, a coupler is provided for coupling together first and second needleless connectors associated with first and second medical fluid flow systems, where each of the needleless connectors includes a housing with a fluid flow path there through terminating at an end opening in a female Luer taper. A resilient valve is disposed within the opening and seals the opening in a first closed position and is compressible to a second open position. The coupler includes an ultraviolet light transmissive housing including opposed male Luer connectors. A fluid flow path extends through the housing and terminates in an end port of each of the male Luer connectors. Each of the opposed male Luer connectors can be connected to the female Luer taper of one of the needleless connectors so as to compress the resilient valve therein to open a flow path between the first and second fluid flow systems through the respective needleless connectors and the coupler.

BRIEF DESCRIPTION OF THE DRAWINGS

FIG. 5C shows the system of FIG. 5B after the irradiation by ultraviolet light has been ceased;

DETAILED DESCRIPTION OF EMBODIMENTS

Figure 1:
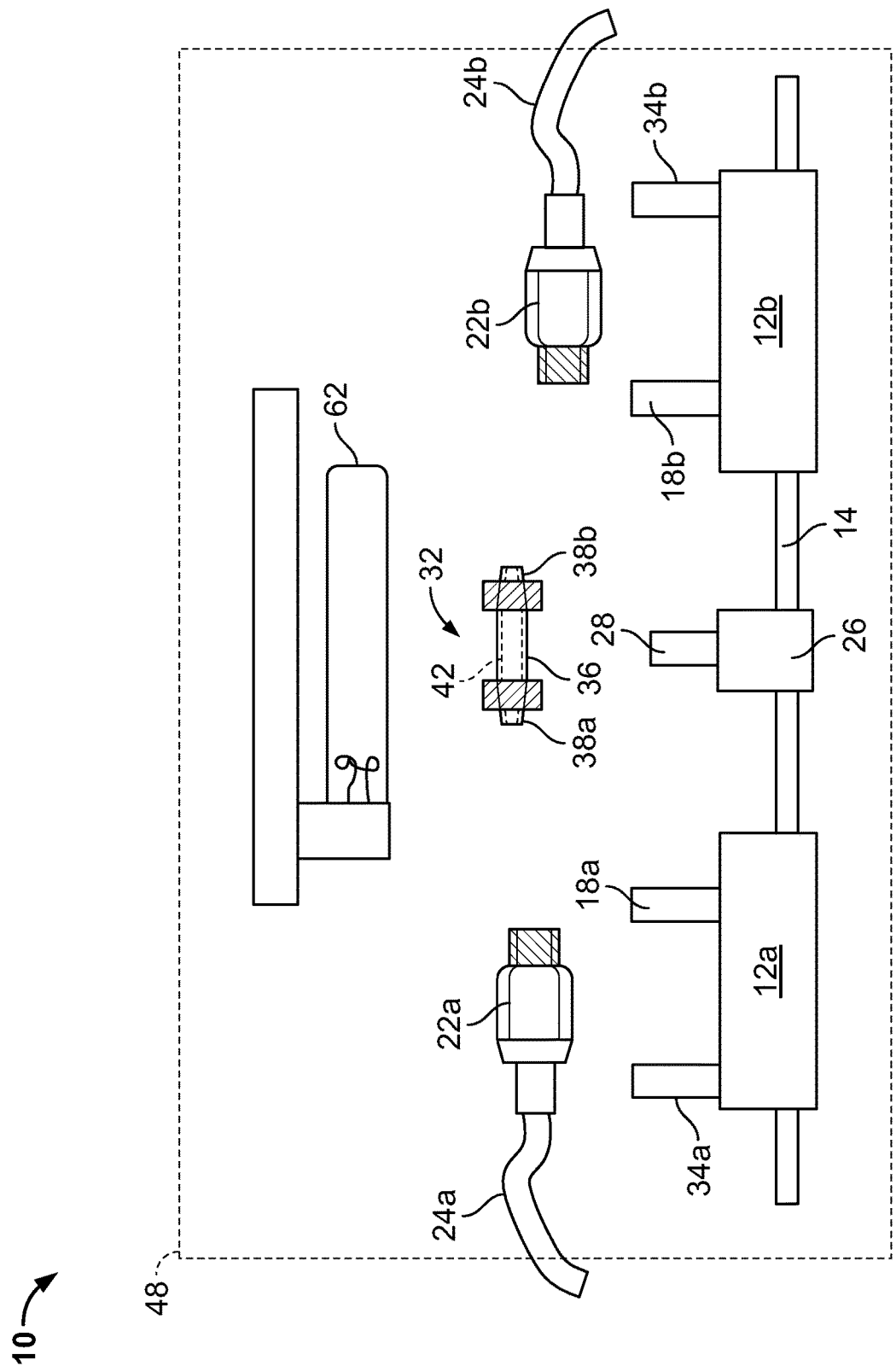
FIG. 1 is a side elevational view of an embodiment of the system of the disclosure with the two connectors and coupler just prior to loading.
Figure 2:
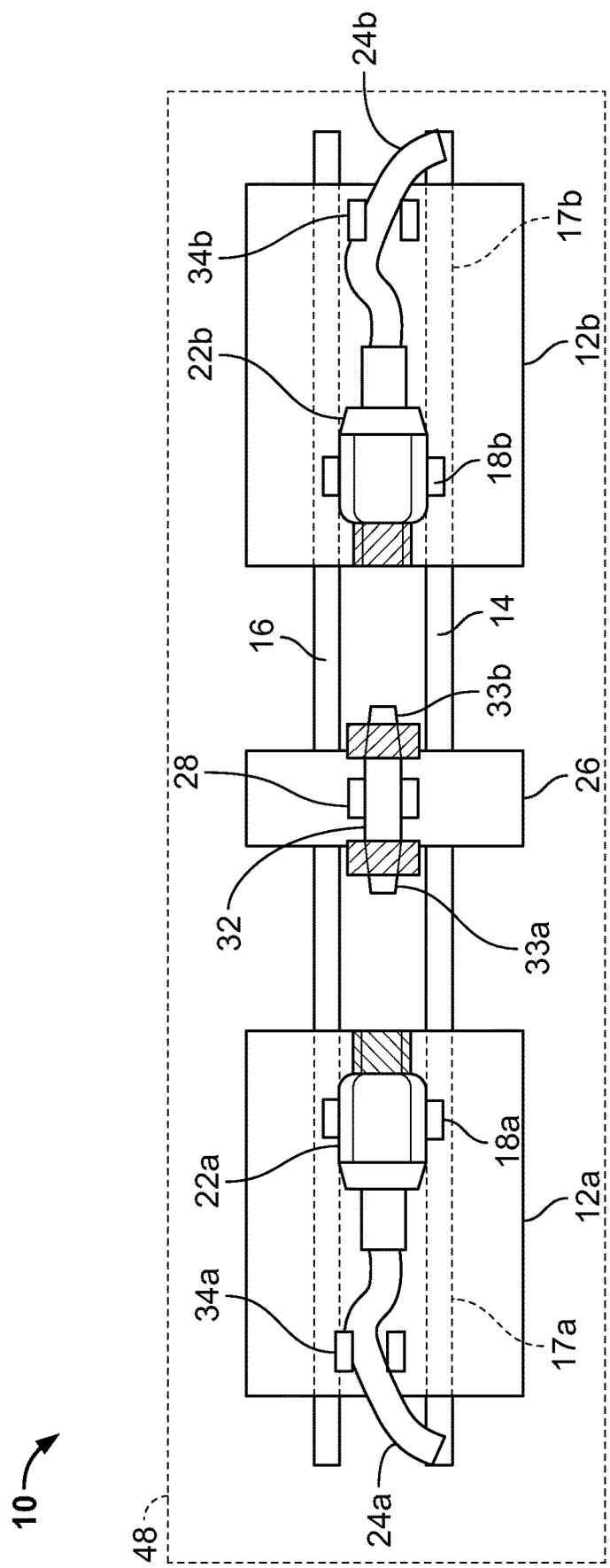
FIG. 2 is a top plan view of the system of FIG. 1 with the ultraviolet light source omitted for clarity.

One embodiment of the device or system of the disclosure is indicated in general at 10 in FIGS. 1 and 2. A linear movement carriage system includes a pair of connector holders 18a and 18b located on carriages 12a and 12b. Carriages 12a and 12b are slidably mounted on a guide, such as guide rails 14 and 16. More specifically, each carriage includes a pair of bores, illustrated in phantom at 17a and 17b in FIG. 2, through which the rails 14 and 16 pass. The guide may alternatively take the form of a channel formed in a base that supports the components of the device. The channel may be sized to slidably receive the carriages. As another example, the guide may take the form of a pair of rails that engage the sides of the carriages as they slide. As yet another example, the guide may be a track positioned on the base. Any other guide arrangement known in the art may alternatively be used.

The carriages are provided with holders, such as, for example, clamps 18a and 18b that, as explained in greater detail below, are configured to removably receive a first needleless connector 22a and a second needleless connector 22b. Clamps 18a and 18b may be of any suitable construction but preferably are constructed from substantially rigid material with each including a pair of opposing, curved jaws that can flex so that a connector is received there between in a snap fit fashion. Alternatively, the clamps 18a and 18b may each include a pair of jaws or other gripping members that are motorized so as to spread apart and/or move together, to hold a connector, as a motor is energized. Any other clamping or holding arrangement known in the art could alternatively be used.

As illustrated, tubing 24a and 24b are each part of, respectively, first and second medical fluid flow systems. Each is attached to one of the connectors 22a and 22b, respectively. The other ends of the tubing (not shown) may each terminate in a container for holding blood, medicine or other chemical, a disposal system, a processing system or any other component of a medical fluid flow system.

A coupler holder 26 is positioned between the sliding carriages, preferably, but not exclusively, in a fixed fashion. Similar to carriages 12a and 12b, the coupler holder 26 may include a clamp 28 or other structure for holding a coupler, indicated in general at 32. Illustrated clamp 28 preferably is constructed from substantially rigid but somewhat flexible material and includes a pair of opposing, curved jaws or other gripping members so that the coupler is received there between in a snap fit fashion. Alternatively, the clamp 28 may include a pair of jaws that are motorized so as to spread apart and/or move together to hold the coupler as a motor is energized. Any other clamping or holding arrangement known in the art could alternatively be used.

A tubing clamp 34a is provided on carriage 12a and a tubing clamp 34b is provided on carriage 12b. The tubing clamps may be mounted in alternative locations, as long as they are capable of receiving tubing 24a and 24b and accommodating movement of the carriages. As described in greater detail below, the tubing clamps 34a and 34b include facing jaws that are articulated by an actuator to engage or pinch and close off tubing 24a and 24b, respectively to fluid flow. The tubing clamp actuator may optionally include a solenoid so as to be electronically actuated. Examples of suitable tubing clamp actuators are provided in U.S. Pat. No. 2,645,245 to Maisch; U.S. Pat. No. 3,075,551 to Smith et al.; U.S. Pat. No. 4,524,802 to Lawrence et al.; U.S. Pat. No. 5,188,334 to Yoshii et al.; and U.S. Pat. No. 9,022,344 to Manzella Jr. et al., the contents of each of which is hereby incorporated by reference. Alternative actuators known in the art may also be used for tubing clamps 34a and 34b.

With reference to FIG. 1, coupler 32 preferably includes a body or housing having a middle portion 36 and opposite ends terminating in male Luer taper connectors 38a and 38b. A fluid flow path, illustrated in phantom at 42 in FIG. 1, extends through the coupler body and communicates with end ports at the end of each male Luer connector. The coupler may be of rigid plastic material and transparent to ultraviolet light, allowing ultraviolet exposure to sterilize the inner fluid flow path 42.

Needleless connectors 22a and 22b each preferably includes a housing with a fluid flow path passing through it that communicates with the fluid flow path of the corresponding tubing. The fluid flow path of each connector preferably terminates at an end opening in a female Luer taper with a resilient valve positioned therein. The resilient valve seals the opening in a closed position and is compressible to an open position. Examples of suitable connectors include, but are not limited to, the connectors disclosed in U.S. Pat. No. 5,047,021 to Utterberg; U.S. Pat. No. 5,700,248 to Lopez; U.S. Pat. No. 5,820,601 to Mayer; U.S. Pat. No. 6,113,068 to Ryan; U.S. Pat. No. 6,569,125 to Jepson et al.; U.S. Pat. No. 7,998,122 to Lynn et al.; U.S. Pat. No. 8,152,790 to Lopez et al. and U.S. Pat. No. 8,277,424 to Pan and U.S. Patent Application Publication No. US 2012/

0089086 to Hokanson, the contents of each of which is hereby incorporated by reference.

Figure 3:
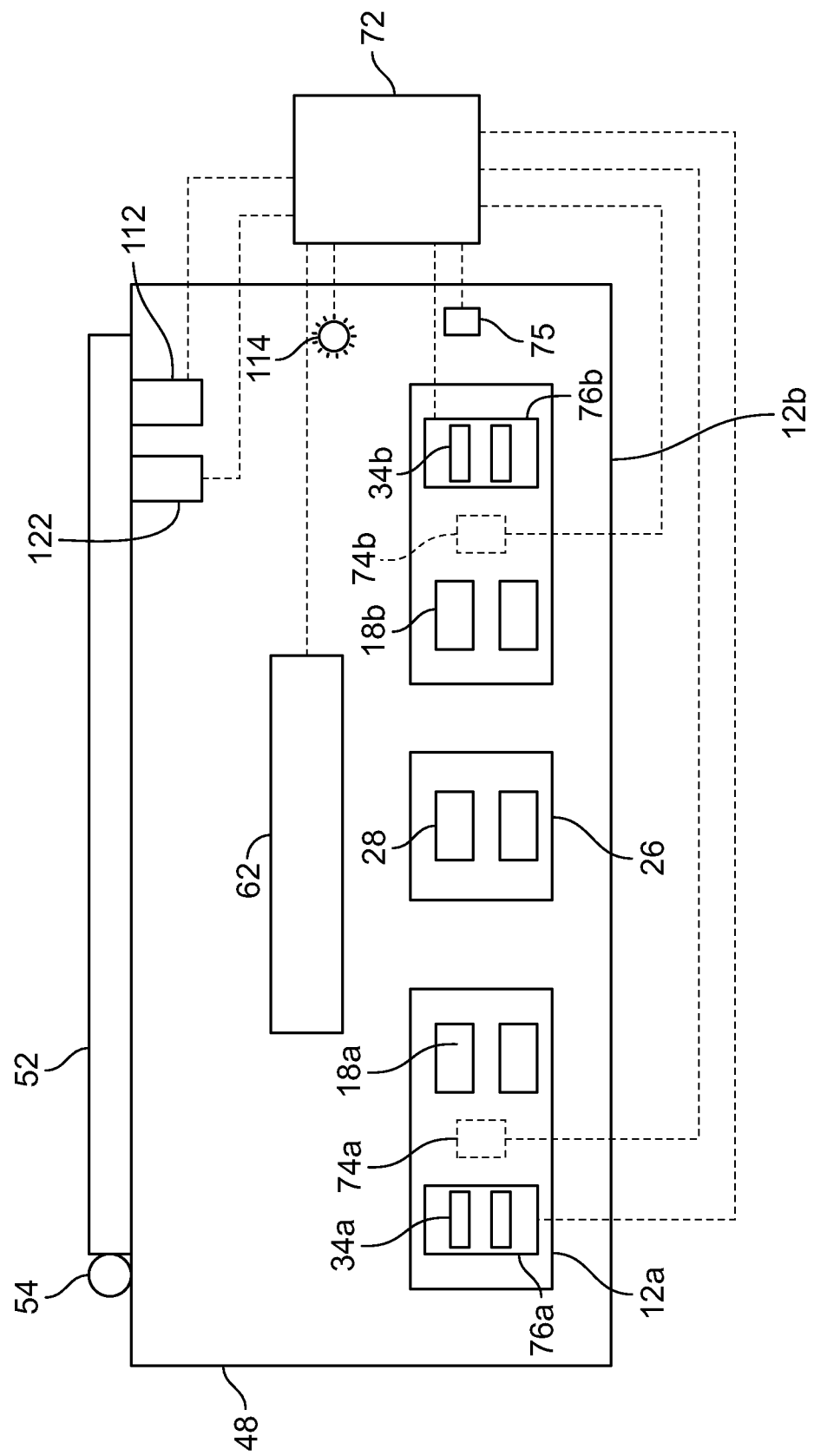
FIG. 3 is a schematic of the components and the control system of an embodiment of the system of the disclosure.

The above components are mounted within a housing of any suitable shape, as indicated at 48 in FIGS. 1-3. The housing is constructed from a material that is substantially non-transmissive of ultraviolet light. As illustrated in FIG. 3, the housing may have a lid or door 52 that covers an opening that provides access to the interior of the housing, and thus enables the connectors (22a and 22b of FIGS. 1 and 2) and coupler (32 of FIGS. 1 and 2) to be inserted and removed. The tubing attached to the connectors may be accommodated by slits or holes formed in opposite ends of the door or housing. The housing door may be pivotally mounted to the housing by a hinge 54 (FIG. 3) or the door or lid may simply lift off of the housing or otherwise be secured to the housing in a removable or opening fashion using arrangements known in the art.

The housing preferably includes an ultraviolet light reflecting interior surface which may, for example, be provided by an ultraviolet light reflective coating formed from, for example, aluminum.

Tubing clamps 34a and 34b may optionally be positioned external to the housing 48.

An ultraviolet light source in the form of an ultraviolet light bulb 62 is also positioned within the housing, as illustrated in FIGS. 1 and 3. The ultraviolet light source preferably provides ultraviolet C (UV-C) light, which is known for use in ultraviolet germicidal irradiation (UVGI) systems to provide short-wavelength ultraviolet light that kills or inactivates microorganisms. As an example only, the light source preferably emits ultraviolet light with wavelengths in the range of 250-280 nm.

As will be described in greater detail below, the light source is used to irradiate the connectors and the coupler to sterilize them as they are connected. In addition to the housing being made from a material that is substantially non-transmissive of ultraviolet light, the slots or openings at the ends of the housing or door are preferably adapted to engage or optically seal around the tubes to prevent the escape of UV-C light. Examples of suitable ultraviolet housing designs are provided in the aforementioned U.S. Pat. No. 4,500,788 to Kulin et al.; U.S. Pat. No. 4,503,333 to Kulin et al. and U.S. Pat. No. 4,882,496 Bellotti et al., the contents of each of which is hereby incorporated by reference.

The coupler 32 (FIGS. 1 and 2) is made of ultraviolet light transparent or transmissive material to enable the flow path of the coupler (42 in FIG. 1) to be irradiated with the UV-C light. Basically any rigid or at least semi-rigid UV-C light transparent material known in the art may be used to construct the coupler. Examples of suitable materials include polychlo otrifluoroethylene (PCTFE), quartz glass, cyclic olefin copolymer (COC polymer) or a formulation of polymethylmethacrylate.

The ultraviolet light source intensity, the proximity of the light source to the coupler and connectors and the ultraviolet transmission capability of the coupler material all may be chosen to dose the interior surfaces of the coupler with about 5 mJ/cm2 of UV-C light or greater.

An example of a control system for operating the device 10 of FIG. 1 is presented in FIG. 3. The carriages 12a and 12b are each provided with a drive system that includes a motor 74a and 74b, respectively. A controller 72, which may be a microprocessor or other electronic control device known in the art, electrically communicates with the light source 62, carriage motors 74a and 74b, a "Start" switch 75 and mechanisms 76a and 76b for actuating tubing clamps 34a and 34b, respectively.

Operation of the device will now be described with reference to FIGS. 3, 4 and 5A-5D. After the housing door is opened, the connectors 22a and 22b are placed in connector holder clamps 18a and 18b and the UV-C transmissive coupler 32 is placed in coupler holder clamp 28, as illustrated in FIG. 5A. In addition, tubing 24a and 24b is positioned with tubing clamps 34a and 34b, which are in the open configuration. The user then closes the housing lid.

Figure 4:
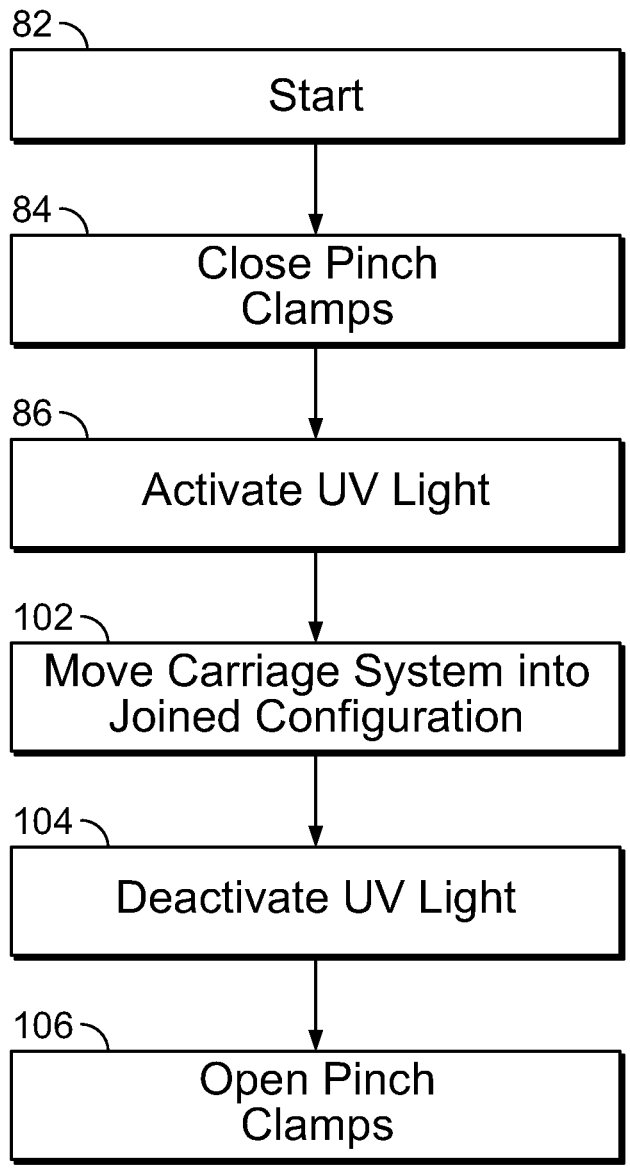
FIG. 4 is a flow diagram illustrating processing performed by the control system of FIG. 3 in accordance with an embodiment of the method of the disclosure.
Figure 5A:
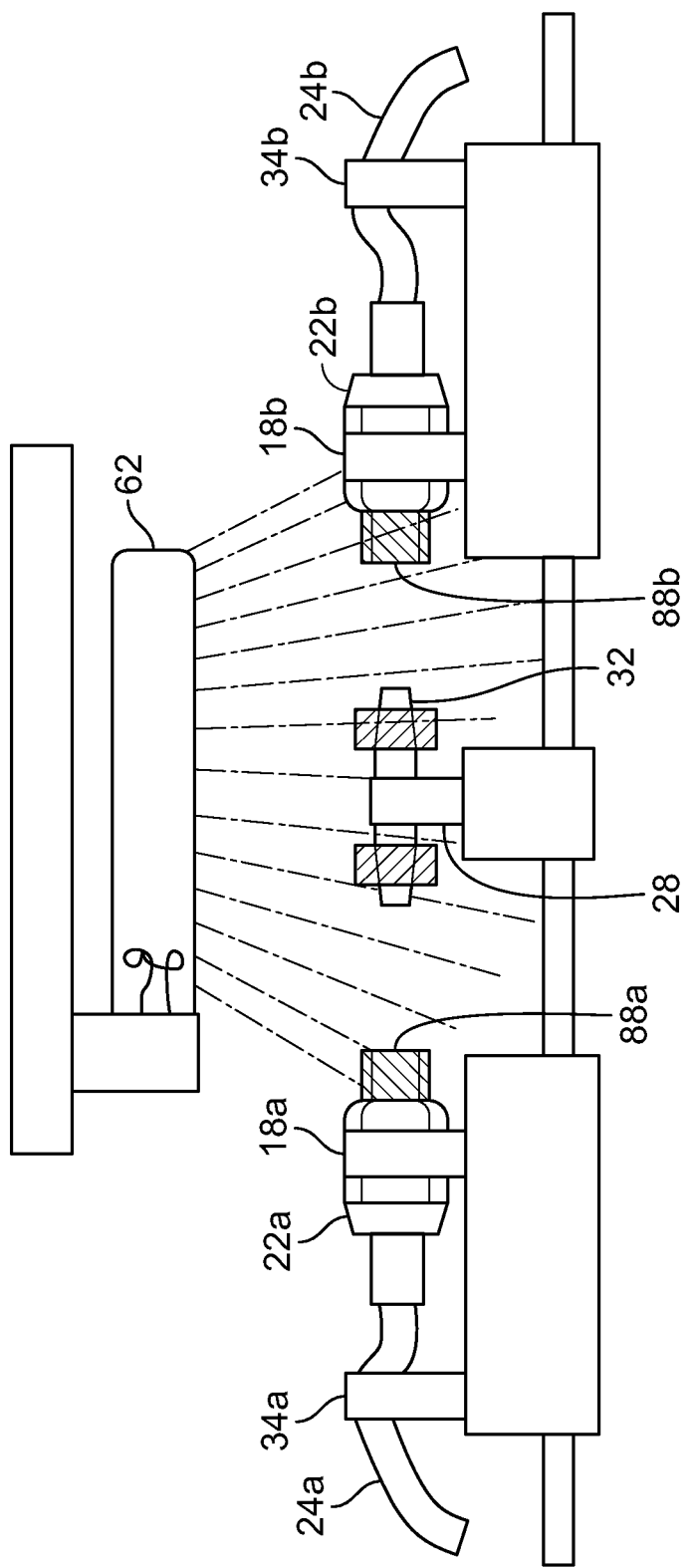
FIG. 5A shows the system of FIG. 3 prior to connecting or joining the two loaded connectors to the loaded coupler and during irradiation by ultraviolet light.

To initiate the sterilization and connection process, as indicated by block 82 of FIG. 4, the user pushes the Start button (75 of FIG. 3). In response, as indicated by block 84 of FIG. 4, the controller (72 of FIG. 3) closes the tubing clamps 34a and 34b so that the flow paths of the tubing 24a and 24b upstream and downstream of the connectors are pinched closed. This reduces the risk of substantial leakage during the mating of the Luer connectors.

As indicated at step 86 of FIG. 4, the controller then activates the UV-C light source. As a result, with reference to FIG. 5A, the external vertical surfaces of the connector valves, illustrated at 88a and 88b, are irradiated with UV-C light from light source 62. Since the needleless female Luer connectors 22a and 22b maintain sterility of the upstream and downstream connector and tubing fluid paths, only the connector valve exterior surfaces require UV-C light dosing.

Furthermore, as illustrated in FIG. 5A, coupler 32 is irradiated with UV-C light. As a result of the construction of the coupler from UV-C light transmissive material, both the exterior surfaces of the coupler and the interior surface of the fluid flow path 42 therethrough are irradiated with the UV-C light. This results in assembly where the surfaces involved in making the connections, i.e. the exterior surface of the female Luer connectors and the exterior and interior surfaces of the coupler are reliably sterile without the need for meticulous manual swabbing.

The connectors and coupler are irradiated for a period of time prior to being joined to ensure that enough dosage of UV-C light is delivered to adequately sterilize the inner and outer surfaces of the coupler and the exterior surfaces of the connector valves.

Figure 5B:
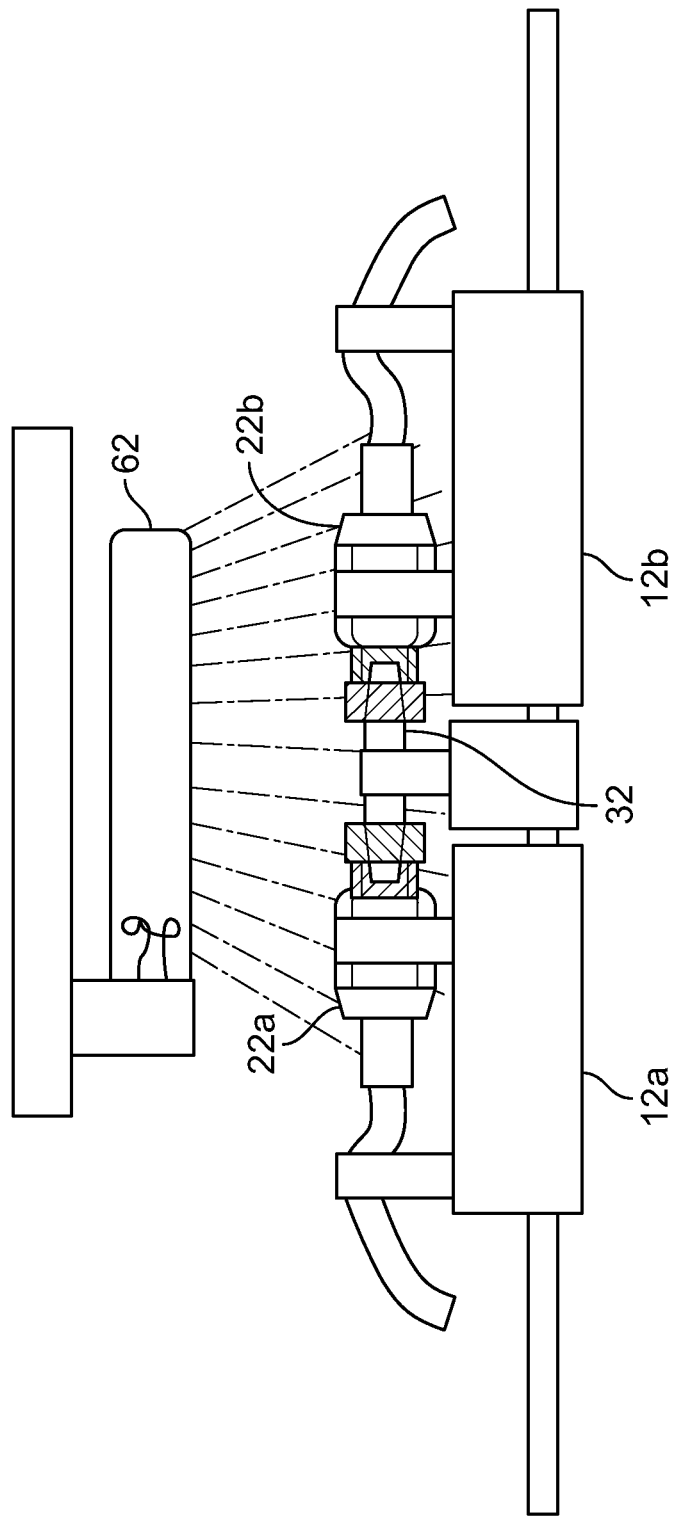
FIG. 5B shows the system of FIG. 5A after the two connectors have been joined to the coupler and during continued irradiation by ultraviolet light.

Next, with reference to FIG. 3, the controller 72 activates the motors 74a and 74b of the carriages 12a and 12b so that the connectors 22a and 22b are moved towards the coupler 32. This movement continues until the connectors connectively engage or are joined to the coupler 32. As this occurs, the male Luer tapers of the coupler (38a and 38b of FIG. 1) move into the female Luer tapers and open the valves of the connectors 22a and 22b so that fluid flow paths of the connectors are in communication with the fluid flow path of the coupler. This step is indicated by block 102 of FIG. 4 and is illustrated in FIG. 5B. The movement continues until the male Luer surfaces are in tight engagement with the matching female Luer taper.

A variety of electromechanical systems known in the art may be used to move the carriages 12a and 12b. For example, carriage motors 74a and 74b may take the form of piezoelectric motors that are mounted to the carriages and that engage guide rails 14 and 16 (FIG. 2) so as to move the carriages towards the coupler holder when energized. As another example, the motors 74a and 74b may be electric motors that are mounted to the housing or a base of the device independent of the carriages. A leadscrew may be attached to the driveshaft of each motor, with the leadscrew oriented with its longitudinal axis parallel to the direction of carriage travel, and each leadscrew may engage a threaded bore of a corresponding carriage so that the carriages are slid towards the coupler when each motor is energized.

As illustrated in FIG. 5B, dosing or irradiation of the connectors and coupler by the UV-C light source 62 continues as the connectors 22a and 22b are joined to the coupler 32 to ensure a contamination-free connection.

As noted above, tubing 24a and/or 24b may be attached to a bag or other container holding blood, medicine or other fluid flow system component. Such containers may be pressurized or elevated so that liquid will flow through a corresponding connector 22a and/or 22b when the connector valve is opened. The closed configuration of the tubing clamps 34a and 34b prevents such liquid flow from occurring and prevents significant leakage from between the pinched portion of the tubing and a corresponding connector when the connector valve is opened by the coupler during the joining step.

Turning to FIG. 5C, after the connectors 22a and 22b are joined to the coupler 32, the UV-C light source 62 is deactivated by the system controller (see step 104 of FIG. 4). The intensity of the UV-C light source is preferably at a level that an irradiation time (including both prior to and after joining of the components) of 20 seconds or less is necessary to obtain satisfactory sterilization. Even more preferable is an irradiation time of less than 10 seconds.

As illustrated at step 106 of FIG. 4, the controller next activates tubing clamp actuators (76a and 76b of FIG. 3) to open the tubing pinch clamps so that fluid flow through the fluid paths of the tubing, connectors and coupler occurs.

Figure 5D:
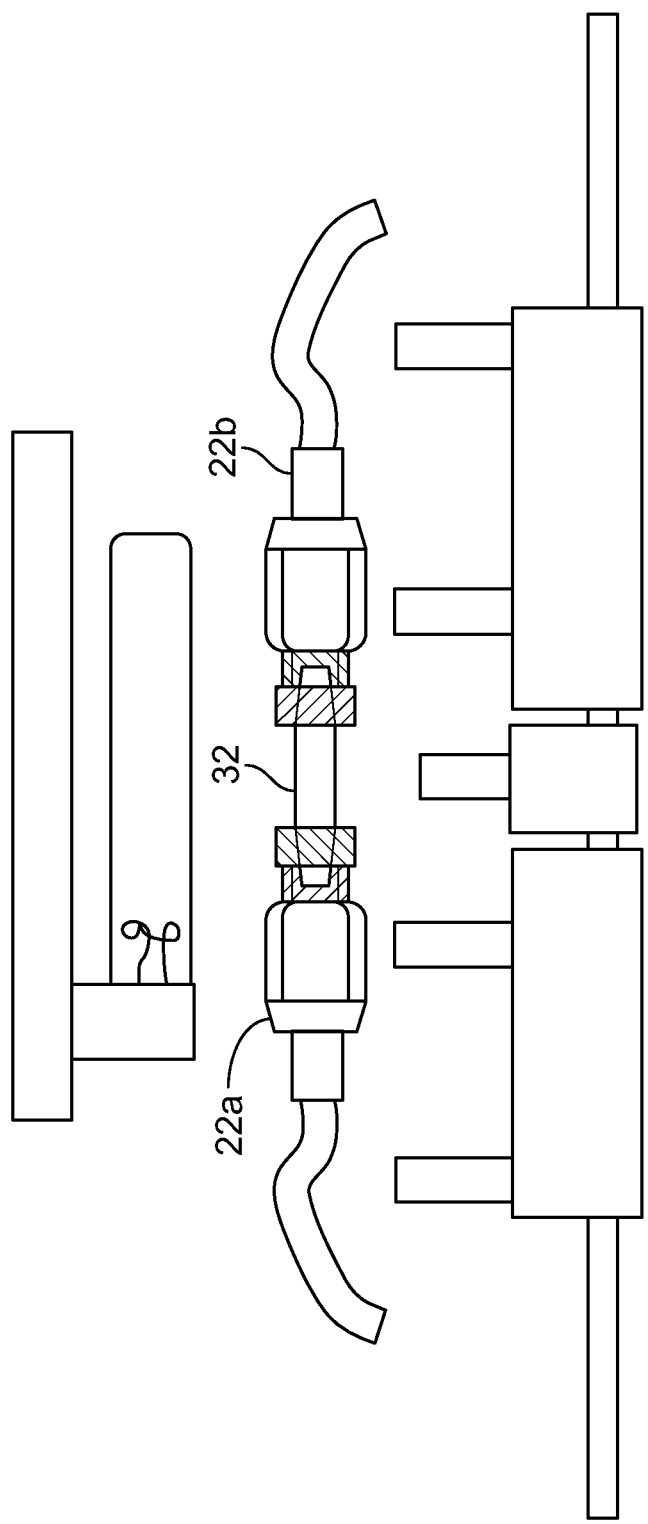
FIG. 5D shows the system of FIG. 5C with the joined connectors and coupler being removed.

The housing door may then be opened, and the connected coupler 32 and connectors 22a and 22b removed from the holders and housing, as illustrated in FIG. 5D.

Alternatively, for connections between the coupler and connectors that may be temporary, the joined coupler and connectors may remain in the housing (with the housing door closed) until the fluid transfer is complete. In the event that the user wishes to preserve the sterility of the connector and coupler components and the associated fluid pathway for further use, after fluid transfer is complete, the tubing clamps 34a and 34b may again be closed and the UV-C light source 62 reactivated. The carriage drive system may then be activated by the controller so as to move the connector carriages away from the coupler holder towards the positions illustrated in FIG. 5A. The UV-C light source may then be deactivated. Such a procedure and embodiment enables reconnecton of the components at a later time so as to make the coupler and connectors available for multiple uses.

As illustrated in FIG. 3, controller 72 may also communicate with a proximity sensor 112 as well as a warning light 114 that is positioned on, or close to, the device housing 48. Proximity sensor 112 is configured to detect the proximity of the housing door 52 when in the closed position (illustrated in FIG. 3) and to send a signal to the controller when the door is open. In this regard, the controller performs the processing illustrated in FIG. 6. More specifically, as indicated by step 116, the controller checks if the door of the housing is closed by monitoring the proximity sensor. If the proximity sensor indicates that the door is open, the controller deactivates the UV-C light source, as indicated by step 118. In addition, as indicated by step 120 the controller may illuminate the warning light (114 of FIG. 3) to further indicate that the door is ajar.

In an alternative embodiment, with reference to FIG. 3, the controller 72 may communicate with a locking mechanism 122 that prevents the housing door from being opened. In such an embodiment, the controller performs the processing illustrated in FIG. 7. This processing is identical to the processing of FIG. 4 with the exception of the addition of steps 124 and 126. In accordance with the method of FIG. 4, after the two connectors and coupler have been loaded into the holders within the device housing, and the door closed, the user presses the "Start" button (75 of FIG. 3). The controller then activates the door locking mechanism (122 of FIG. 3), as indicated by step 124 of FIG. 7. The device then continues to operate as described above until the tubing clamps are opened after the sterilization and connecting or joining steps. After the tubing clamps are opened, as indicated at step 126 in FIG. 7, the controller deactivates the door locking mechanism so that the user may open the housing door and remove the joined connectors and coupler.

Figure 6:
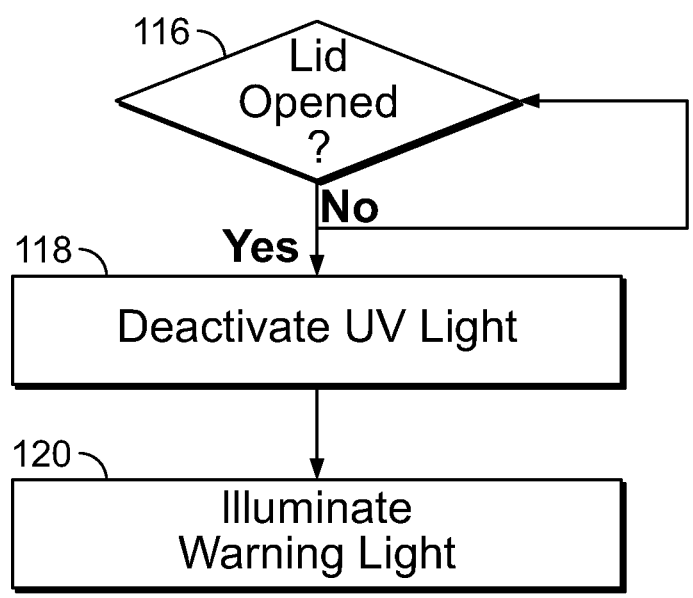
FIG. 6 is a flow diagram illustrating processing performed by the control system of FIG. 3 to monitor the configuration of the housing door.
Figure 7:
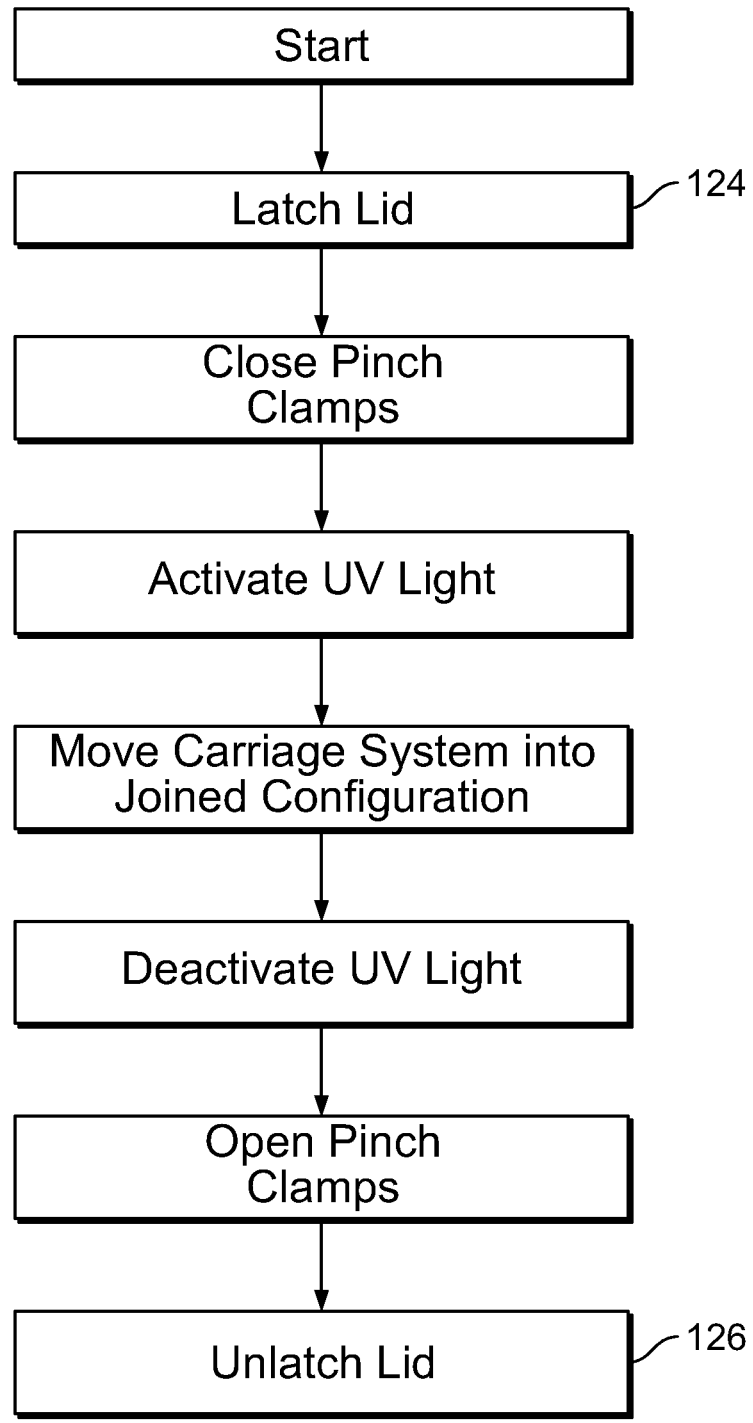
FIG. 7 is a flow diagram illustrating processing performed by the control system of FIG. 3 in accordance with another embodiment of the method of the disclosure.

In still another embodiment, the device may be provided with both the proximity sensor 112 and the door locking mechanism 122 of FIG. 3 so that the processing of both FIGS. 6 and 7 is performed by the controller.

Figure 8:
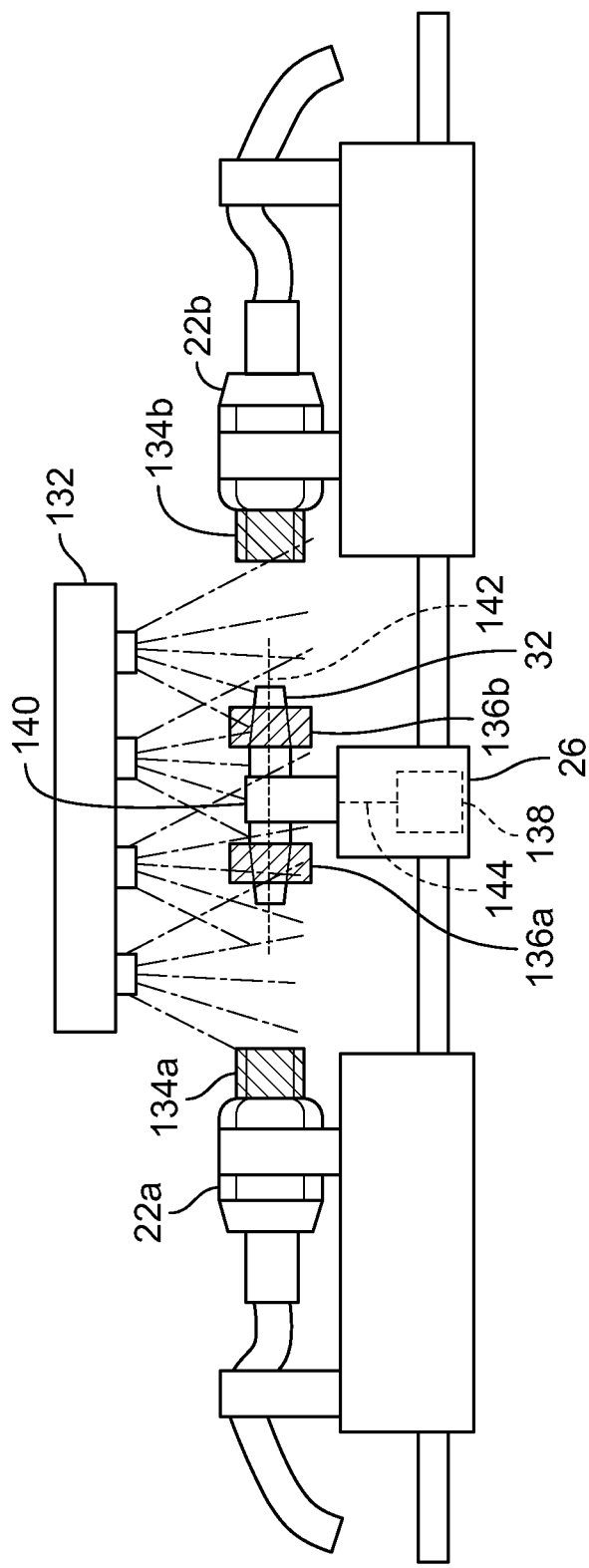
FIG. 8 is a side elevational view of an alternative embodiment of the system of the disclosure where ultraviolet light emitting diode emitters are used.

In a further alternative embodiment, illustrated in FIG. 8, the ultraviolet light bulb 62 (of FIGS. 1 and 5A-5D) may be replaced with light emitting diode emitters 132. The light emitting diode emitters 132 of FIG. 8 irradiate the ultraviolet transparent coupler 32 and connectors 22a and 22b with UV-C light in the manner described above with reference to FIGS. 5A-5D. Such light emitting diode emitters offer advantages over the UV-C light bulb of FIGS. 5A-5D in that some versions may be battery powered.

With continued reference to FIG. 8, the exterior surfaces of the distal ends of connectors 22a and 22b may be provided with threads 134a and 134b. When such connectors are used, ultraviolet light transparent coupler 32 may be provided with collars 136a and 136b that define annular spaces surrounding the ends of the coupler. The inner surfaces of the collar are provided with threads that mate with the threads 134a and 134b of the respective connectors. When such connectors and coupler are used, coupler holder 26 is preferably provided with a motor 138 and the coupler holder 140 is preferably adapted to rotate the coupler about an axis, indicated at 142, so that the coupler and connector threads engage. A drive mechanism 144 joins the motor 138 to the coupler holder 140 so that the coupler is rotated about the axis 142 when the motor is energized or activated. Suitable motors, holders and drive mechanisms are known in the art.

Figure 9A:
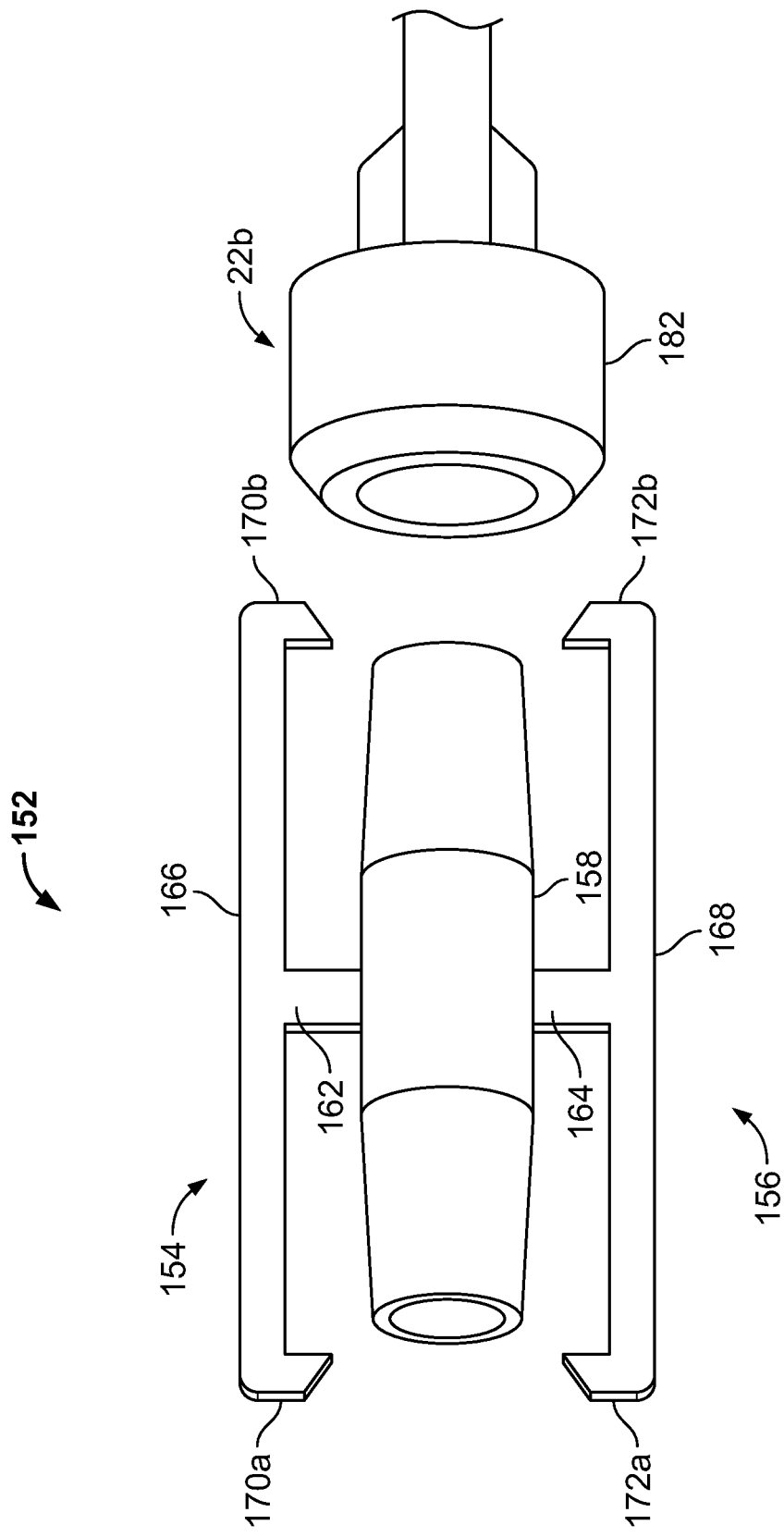
FIG. 9A is an enlarged perspective view of an alternative embodiment of the coupler and one of the connectors prior to being joined.
Figure 9B:
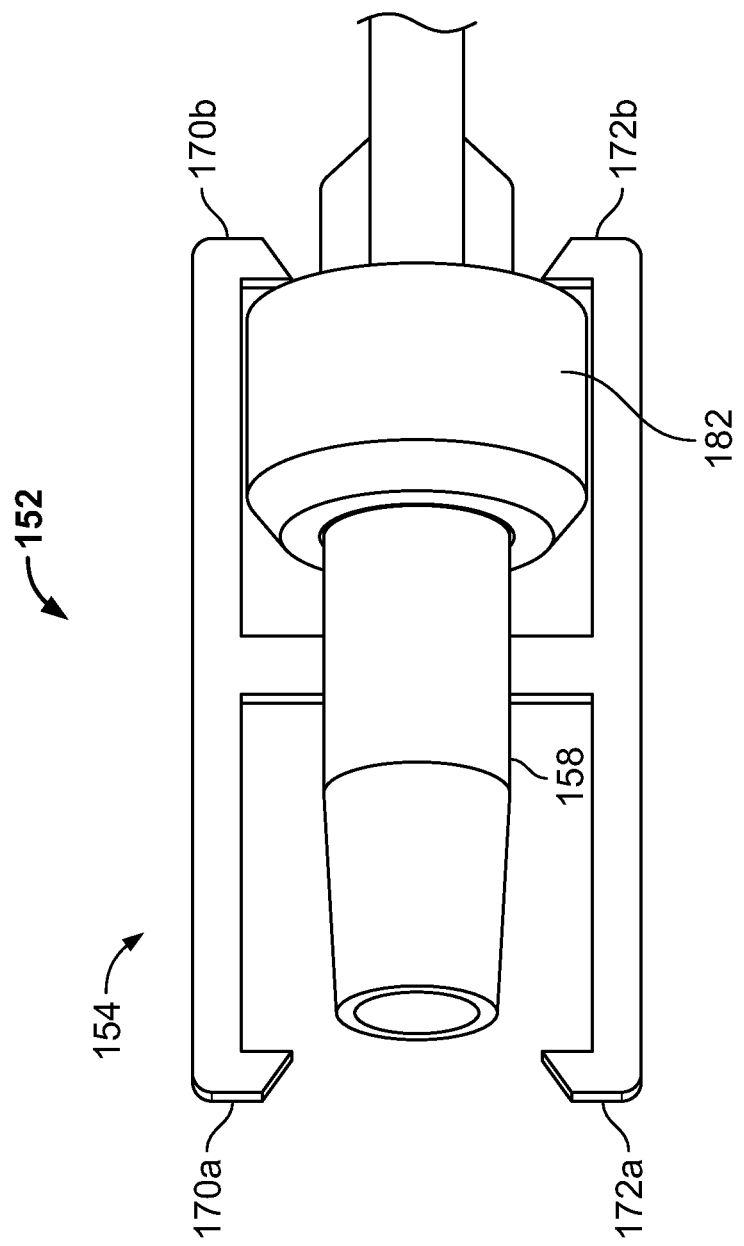
FIG. 9B is a perspective view of the coupler and connector of FIG. 9A after being joined.

In an alternative embodiment, with reference to FIGS. 9A and 9B, the coupler, indicated in general at 152, may be provided with a pair of resilient lever arms, indicated in general at 154 and 156. The lever arms are joined to the housing 158 of the coupler by supports 162 and 164 that bisect elongated members 166 and 168. Elongated member 166 terminates in hooked ends 170a and 170b, while elongated member 168 terminates in hooked ends 172a and 172b. As an example only, the two resilient lever arms may be constructed of the same material as the coupler and integrally formed with the coupler. While two resilient lever arms are illustrated, the coupler may alternatively feature a single resilient lever arm or more than two lever arms. With reference to FIGS. 9A and 9B, connector 22b is provided with a collar 182, while connector 22a (FIG. 1) is provided with a similar collar.

As illustrated in FIGS. 9A and 9B, during the joining step (FIG. 5B, block 102 of FIG. 4), the collar 182 of connector 22b is received and engaged by the hooked ends 170b and 172b of the resilient lever arms. The hooked ends 170a and 172a receive and engage the collar of connector 22a (FIG. 1) in a similar fashion. As a result, the connectors and coupler are joined in a more robust fashion so as to prevent decoupling if the joined components are removed from the device housing.

In another alternative embodiment, the coupler may be provided with collars (similar as those illustrated in FIG. 8) and the connectors may each be provided with resilient lever arms that engage the coupler collars during the joining step (FIG. 5B, block 102 of FIG. 4). In such an embodiment, the collars of the coupler do not need to be threaded. An example of a suitable connector is presented in U.S. Pat. No. 5,688,254 to Lopez et al., the contents of which are hereby incorporated by reference.

It should be noted that the term "motor" as used to describe the above embodiments may be a mechanism that is manually actuated by the user, as opposed to a motor that is powered, for example, by electricity. For example, the motor could include a crank and gears where the user turns the crank to rotate the gears so that the connector carriages 12a and 12b of FIGS. 5A-5D are moved towards the coupler holder. Examples of such mechanisms are presented in the aforementioned U.S. Pat. No. 4,500,788 to Kulin et al. and U.S. Pat. No. 4,882,496 Bellotti et al.

It should be further noted that the carriage system described above, where both of the connector holders are moved towards the fixed coupler holder, is presented as an example only. Other arrangements where the connector and coupler holders are movable relative to each other may be used. In an alternative embodiment, for example, one of the connector holders could be fixed with respect to the coupler holder and other connector holder movable towards the coupler holder. In such an arrangement, the coupler holder could simply be free to slide along the device guide (such as rails 14 and 16 of FIG. 2) with the movable connector holder contacting and pushing the coupler holder towards the fixed connector holder.

ASPECTS

The present subject includes various aspects, which may be in addition to those set forth above, such as:

Aspect 1. A device for connecting first and second medical fluid flow systems, each of which includes, respectively, first and second connectors connectable to a coupler, the device comprising: a housing that is substantially non-transmissive of ultraviolet light; a linear movement carriage system positioned within the housing and including a first connector holder configured to hold the first connector, a second connector holder configured to hold the second connector and a coupler holder configured to hold the coupler, the coupler holder positioned substantially between the first and second connector holders, the first and second connector holders and the coupler holder being relatively moveable between: a separated configuration where the first and second connector holders and the coupler holder are located in relatively spaced apart positions so that first and second connectors held by the first and second connector holders are spaced apart from a coupler held by the coupler holder; and a joined configuration where the first and second connector holders are positioned more closely to the coupler holder than when in the separated configuration so that the first and second connectors held by the first and second connector holders engage the coupler held by the coupler holder; an ultraviolet light source positioned in the housing so as to irradiate first and second connectors held by the first and second connector holders and a coupler held by the coupler holder when the carriage system is in the separated configuration; and a drive system including a first motor operatively connected to at least one of the first and second connector holders so as to transition the first and second connector holders and the coupler holder between the separated and the joined configurations.

Aspect 2. The device of Aspect 1, wherein the drive system is electromechanical.

Aspect 3. The device of Aspect 1 or 2, wherein the carriage system includes a guide with respect to which the first connector holder is moveably positioned and the first motor is operatively associated with the first connector holder and the guide so as to move the first connector holder along the guide as the carriage system is transitioned between the separated and joined configurations when the first motor is actuated.

Aspect 4. The device of any one of Aspects 1-3, further comprising a leadscrew attached to the first motor so that the leadscrew is rotated about a longitudinal axis when the first motor is actuated, said leadscrew engaging the first connector holder so that the first connector holder is moved when the first motor rotates the leadscrew.

Aspect 5. The device of any one of Aspects 1-4 further comprising a first tubing clamp adapted to receive a first tubing communicating with the first connector, said first tubing clamp being operable to block fluid flow through the first tubing in a closed configuration and to allow fluid flow through the first tubing when in an open configuration.

Aspect 6. The device of Aspect 5 further comprising a first tubing clamp actuator operatively associated with the first tubing clamp to move the first tubing clamp between the closed and open configurations.

Aspect 7. The device of Aspects 5 or 6 further comprising a second tubing clamp adapted to receive a second tubing communicating with the second connector, said second tubing clamp being operable to block fluid flow through the second tubing in a closed configuration and to allow fluid flow through the second tubing when in an open configuration.

Aspect 8. The device of Aspect 7 further comprising a second clamp actuator operatively associated with the second tubing clamp to move the second tubing clamp between the closed and open configurations.

Aspect 9. The device of Aspect 1 wherein the housing defines an interior and further comprising a door moveable between an open configuration, where the interior of the housing may be accessed, and a closed configuration, where the interior of the housing cannot be accessed.

Aspect 10. The device of Aspect 9 further comprising a proximity sensor operable to detect whether the door is in the closed configuration and a controller in communication with the proximity sensor and the ultraviolet light source, said controller adapted to allow power from a power source to the ultraviolet light source when the proximity sensor indicates that the door is in the closed configuration and to prevent power to the light source when the door is in the open configuration.

Aspect 11. The device of any one of Aspects 1-10 wherein the drive system further includes a second motor operatively connected to the second connector holder so as to move the second connector holder as the carriage system is transitioned between the separated and the joined configurations.

Aspect 12. The device of Aspect 11 wherein the coupler holder is in a fixed position with respect to the moveable first and second connector holders.

Aspect 10. A method for connecting first and second medical fluid flow systems, each of which includes, respectively, first and second connectors connectable to a coupler, the method comprising the steps of: positioning the coupler between the first and second connectors in a spaced-apart position within a substantially ultraviolet non-transmissive housing; irradiating the coupler and the first and second connectors with ultraviolet light; relatively moving the first and second connectors and the coupler so that the first and second connectors connectably engage the coupler; and removing the connected first and second connectors and coupler from the housing.

Aspect 14. The method of Aspect 13 wherein the step of relatively moving includes rotating the coupler relative to the first and second connectors.

Aspect 15. The method of Aspect 13 or 14 further comprising closing a first tubing communicating with the first connector and closing a second tubing communicating with the second connector so that no fluid is able to flow through the tubing prior to irradiating and opening the first and second tubing so that fluid is able to flow through each after the first and second connectors are connectably engaged with the coupler.

Aspect 16. The method of any one of Aspects 13-15 wherein the relatively moving includes moving the first and second connector holders toward the coupler holder.

Aspect 17. The method of any one of Aspects 13-16 wherein the coupler has an interior passage and is substantially transmissive of ultraviolet light so that the interior passage of the coupler is irradiated with ultraviolet light during the irradiating Aspect 18. The method of any one of Aspects 13-16 wherein the ultraviolet light is ultraviolet C.

Aspect 19. A coupler for coupling together first and second needleless connectors associated with first and second medical fluid flow systems, each of which needleless connectors comprises a housing with a fluid flow path there through terminating at an end opening in a female Luer taper and a resilient valve disposed within and sealing the opening in a first closed position and being compressible to a second open position, the coupler comprising: an ultraviolet light transmissive housing including opposed male Luer connectors, and a fluid flow path extending through the housing and terminating in an end port of each of the male Luer connectors, whereby each of the opposed male Luer connectors can be connected to the female Luer taper of one of the needleless connectors so as to compress the resilient valve therein to open a flow path between the first and second fluid flow systems through the respective needleless connectors and the coupler.

Aspect 20. The coupler of Aspect 19 including a threaded collar associated with each male Luer connector for threadedly engaging a respective needleless connector connected thereto.

Aspect 21. The coupler of Aspect 19 including a resilient lever arm connected to the housing and having a pair of hooked ends for engaging collars of needleless connectors connected to the male Luer connectors.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. A device for connecting first and second medical fluid flow systems, each of which includes, respectively, first and second connectors connectable to a coupler, the device comprising:
   a. a housing that is substantially non-transmissive of ultraviolet light;
   b. a linear movement carriage system positioned within the housing and including a first connector holder configured to hold the first connector, a second connector holder configured to hold the second connector and a coupler holder configured to hold the coupler, said coupler holder positioned substantially between the first and second connector holders, the first and second connector holders and the coupler holder being relatively moveable between:
      i) a separated configuration where the first and second connector holders and the coupler holder are located in relatively spaced apart positions so that first and second connectors held by the first and second connector holders are spaced apart from a coupler held by the coupler holder; and
      ii) a joined configuration where the first and second connector holders are positioned more closely to the coupler holder than when in the separated configuration so that the first and second connectors held by the first and second connector holders engage the coupler held by the coupler holder;
   c. an ultraviolet light source positioned in the housing so as to irradiate the first and second connectors held by the first and second connector holders and the coupler held by the coupler holder when the linear movement carriage system is in the separated configuration; and
   d. a drive system including a first motor operatively connected to at least one of the first and second connector holders so as to transition at least two of the first and second connector holders and the coupler holder between the separated and the joined configurations.

2. The device of claim 1 wherein the linear movement carriage system includes a guide with respect to which the first connector holder is moveably positioned and the first motor is operatively associated with the first connector holder and the guide so as to move the first connector holder along the guide as the linear movement carriage system is transitioned between the separated and joined configurations when the first motor is actuated.

3. The device of claim 1 further comprising a leadscrew attached to the first motor so that the leadscrew is rotated about a longitudinal axis when the first motor is actuated, said leadscrew engaging the first connector holder so that the first connector holder is moved when the first motor rotates the leadscrew.

4. The device of claim 1 further comprising a first tubing clamp adapted to receive a first tubing communicating with the first connector, said first tubing clamp being operable to block fluid flow through the first tubing in a closed configuration and to allow fluid flow through the first tubing when in an open configuration.

5. The device of claim 4 further comprising a first tubing clamp actuator operatively associated with the first tubing clamp to move the first tubing clamp between the closed and open configurations.

6. The device of claim 4 further comprising a second tubing clamp adapted to receive a second tubing communicating with the second connector, said second tubing clamp being operable to block fluid flow through the second tubing in a closed configuration and to allow fluid flow through the second tubing when in an open configuration.

7. The device of claim 6 further comprising a second clamp actuator operatively associated with the second tubing clamp to move the second tubing clamp between the closed and open configurations.

8. The device of claim 1 wherein the housing defines an interior and further comprising a door moveable between an open configuration, where the interior of the housing may be accessed, and a closed configuration, where the interior of the housing cannot be accessed.

9. The device of claim 8 further comprising a proximity sensor operable to detect whether the door is in the closed configuration and a controller in communication with the proximity sensor and the ultraviolet light source, said controller adapted to allow power from a power source to the ultraviolet light source when the proximity sensor indicates that the door is in the closed configuration and to prevent power to the ultraviolet light source when the door is in the open configuration.

10. The device of claim 1 wherein the drive system further includes a second motor operatively connected to the second connector holder so as to move the second connector holder as the linear movement carriage system is transitioned between the separated and the joined configurations.

11. The device of claim 10 wherein the coupler holder is in a fixed position with respect to the moveable first and second connector holders.

* * * * *